US00PP14755P2

(12) United States Plant Patent
Zary

(10) Patent No.: US PP14,755 P2
(45) Date of Patent: May 4, 2004

(54) FLORIBUNDA ROSE PLANT NAMED 'JACNEWPU'

(50) Latin Name: *Rosa hybrida*
Varietal Denomination: JACnewpu

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,571

(22) Filed: Nov. 19, 2002

(51) Int. Cl.[7] ..... A01H 5/00
(52) U.S. Cl. ..... Plt./149
(58) Field of Search ..... Plt./149, 147, 107

*Primary Examiner*—Bruce R. Campell
*Assistant Examiner*—June Hwu
(74) *Attorney, Agent, or Firm*—Klarquist Sparkman, LLP

(57) ABSTRACT

Floribunda rose plant having novel tan and pink flowers that age increasinly pink; strong citrus fragrance; flowers presented in clusters; vigorous growth; and dark, glossy, green foliage.

1 Drawing Sheet

Genus and species: *Rosa hybrida.*
Variety denomination: 'JACnewpu'.

SUMMARY OF THE INVENTION

The present invention relates to a new and distinct variety of floribunda rose plant named 'JACnewpu' which was originated by me by crossing the variety 'MACnewye,' U.S. Plant Pat. No. 5,428, with the variety 'KEIbian,' U.S. Plant Pat. No. 8,476.

BACKGROUND OF THE INVENTION

The primary objective of this breeding was to produce a new rose variety having the glossy foliage, flower clusters and vigor of the female parent combined with the strong fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Novel tan and pink flowers that age increasingly pink;
2. Strong citrus fragrance;
3. Flowers presented in clusters;
4. Vigorous growth; and
5. Dark glossy green foliage.

Asexual reproduction of this new variety by budding, as performed at Wasco, Calif., shows that the foregoing and all other characteristics and distinctions come true to form and are established and transmitted through succeeding propagations.

COMPARISON WITH PARENTS

The subject variety differs from the female parent in flower color, scent and petal count and differs from the male parent in flower color, flower size, growth habit and petal count.

COMPARISON WITH SIMILAR VARIETY

There is no other rose variety of which I am aware that has the old fashioned form, fragrance and novel flower color of 'JACnewpu.'

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'MACnewye' (U.S. Plant Pat. No. 5,428).
*Pollen parent.*—'KEIbian' (U.S. Plant Pat. No. 8,476).

FLOWER

Observations made from plants beginning at 3 years of age grown in a garden environment at Somis, Calif. in May 2001–May 2002.

Blooming habit: Continuous.
Bud:
*Size.*—About 2.5 cm long when the petals start to unfurl.
*Form.*—The bud form is long and pointed ovoid.
*Color.*—When sepals first divide, bud color is Red Group 47A. When half blown, the upper sides of the petals are Red Purple Group 63B with a margin of Yellow Group 4C on the lower of half of the petal; and the lower sides of the petals are Red-Purple Group 63D with streaks of Yellow Group 4D and a margin of Yellow Group 4D around the lower half of the petal.

*Sepals.*—Color: Upper surface: Green Group 138B except Green Group 138C adjacent the apex on the upper 10%. Often, in bright sunlight there is a strong Greyed-Purple Group 183D anthrocyanin pigmentation. Lower surface: Green Group 137C. Length: 30 mm. Width: 8 mm. Shape: Subulate. Surface texture: Upper surface: Hoary. Lower surface: Glandular. There are three normally to heavily appendaged sepals. There are two unappendaged sepals with hairy edges.

*Receptacle.*—Color: Green Group 137D. Shape: Funnel. Size: Medium, about 8 mm long×6 mm wide. Surface: Smooth.

*Peduncle.*—Length: Medium, averaging about 7–8 cm. Surface: Rough, prickly and glandular. Color: Green Group 137D and often with a strong anthrocyanin pigmentation of Greyed-Purple Group 183D. Strength: Stiff, erect.

Bloom:

*Size.*—Medium. Average open diameter is about 7–8 cm.

*Borne.*—Singly and several together in pyramidal clusters of 3–5 blooms.

*Stems.*—Strength: Strong. Average length is about 30–40 cm.

*Form.*—When first open: Bloom is high centered. Permanence: Flattens, all petals curl quill fashion.

*Petalage.*—Number of petals under normal conditions: 70–80.

*Color.*—The upper sides of the petals are Red-Purple Group 63B on the outer petals changing progressively inwardly to Red Group 54C and then to near Red Group 42D. All upper sides have a margin of Yellow Group 4C on the lower half of the petal. The reverse sides of the petals are Red-Purple Group 63D with streaks of Yellow Group 4D and a margin of Yellow Group 4D around the lower half of the petal. The base of each petal has an area approximately 5 mm×8 mm of Yellow Group 4B. The major color on the upper side is Red Group 54C.

*Variegations.*—Occasional yellow streaks on the upper and lower surface of the petals.

*Discoloration.*—The general tonality at the end of the first day: No change. At the end of the third day: Slight change to Red-Purple Group 63B across the whole flower. By day five, the color fades to Red-Purple Group 63C. Petals drop day six.

*Fragrance.*—Strong, citrus.

Petals:

*Texture.*—Smooth.

*Shape.*—Orbicular to spatulate.

*Size.*—Width: 2–2.5 cm. Length: 3–3.5 cm.

*Margin.*—Entire. Apex Shape: Rounded to obcordate. Base Shape: Rounded.

*Form.*—Tips slightly recurved, heavily quilled.

*Arrangement.*—Quartered.

*Petaloids.*—Number: 3–7. Color: Red Group 42D. Size: Width: 1–1.5 cm. Length: 2.5–3.0 cm. Shape: Gladiate.

*Persistence.*—Petals drop off cleanly before drying.

*Lastingness.*—On the plant: Long (about 5–6 days). As a cut flower: Fair (about 6–7 days).

Reproductive parts:

*Stamens.*—Number: 40–50. Length: 13 mm. Anthers: Length: 3 mm. Color: Yellow-Orange Group 22C. Filaments: Color: Yellow Group 13B. Length: 10 mm. Pollen: Color: Yellow-Orange Group 22B.

*Pistils.*—Number: 35–40. Styles: Color: Greyed-Green Group 193C. Length: 8–9 mm. Stigmas: Color: Greyed-Purple Group 184A. Length: 1 mm.

*Hips.*—None observed.

Plant:

*Form.*—Bush.

*Growth.*—Vigorous, upright and branching.

*Age to maturity.*—Two years.

*Mature plant.*—Height: 100–120 cm. Width: 70–80 cm.

*Rootstock.*—Dr. Huey.

Foliage: Number of leaflets on normal mid-stem leaves: 5–7.

*Size.*—Medium (10–12 cm long×9–10 cm wide).

*Quantity.*—Abundant.

*Color.*—New foliage: Upper side: Greyed-Red Group 181A with Yellow-Green Group 144D in the center. Lower side: Same as upper. Old foliage: Upper side: Green Group 139A. Lower side: Green Group 137A.

Leaflets:

*Size.*—About 5 cm long×3.5 cm wide.

*Shape.*—Ovate.

*Base shape.*—Rounded.

*Apex shape.*—Acuminate.

*Texture.*—Upper side: Glossy, lustrous.

*Edge.*—Serrated.

*Serrations.*—Single, small.

*Petiole.*—Color: Yellow-Green Group 145B.

*Petiole rachis.*—Color: Yellow-Green Group 145B. Underside: with prickles.

*Auricle shape.*—None.

*Stipules.*—Length: 22 mm. Width: 4 mm. Shape: Linear. Color: Upper surface: Green Group 139A. Lower surface: Green Group 137A.

*Disease resistance.*—Susceptible to mildew and blackspot and resistant to rust under normal growing conditions.

*Pest resistance.*—Not tested.

*Vein color.*—Yellow-Green Group 145B.

*Venation pattern.*—Reticulate.

Wood:

*New wood.*—Color: Greyed-Purple Group 183B. Bark: Smooth.

*Old wood.*—Color: Green Group 137A. Bark: Smooth.

Prickles:

*Quantity.*—On main canes from base: Ordinary (8–9 every 15 cm). On laterals from main canes: Ordinary.

*Form: Hooked downward.*

*Length:* 7–9 mm.

*Color when young: Greyed-Purple Group* 183A.

*Color when mature: Greyed-Orange Group* 177A.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its novel tan and pink flowers that age increasingly pink; strong citrus fragrance; flowers presented in clusters; vigorous growth; and dark, glossy, green foliage.

* * * * *

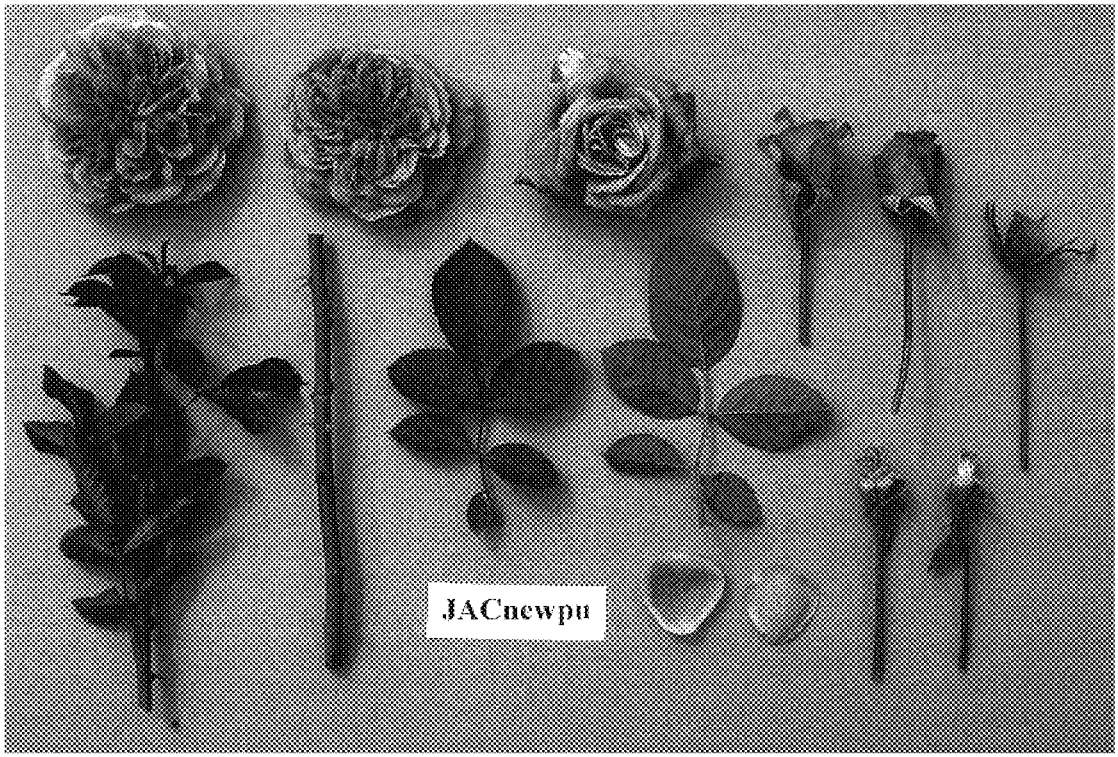
JACnewpu